(12) United States Patent
DesLauriers et al.

(10) Patent No.: US 6,632,680 B1
(45) Date of Patent: Oct. 14, 2003

(54) MEASUREMENT OF SHORT CHAIN BRANCHING IN OLEFIN COPOLYMERS USING CHEMOMETRIC ANALYSIS

(76) Inventors: Paul J. DesLauriers, 1031 Kings Cir., Bartlesville, OK (US) 74006; David C. Rohlfing, 1208 Melmart, Bartlesville, OK (US) 74006; Alan D. Eastman, 550 SE. 16th St., Bartlesville, OK (US) 74003; Eric T. Hsieh, 401161 W. 2460 Dr., Bartlesville, OK (US) 74006

( * ) Notice: Subject to any disclaimer, the term of this patent is extended or adjusted under 35 U.S.C. 154(b) by 0 days.

(21) Appl. No.: 09/667,657

(22) Filed: Sep. 22, 2000

(51) Int. Cl.$^7$ ............................................. G01N 33/44
(52) U.S. Cl. .......................... 436/85; 436/164; 436/171
(58) Field of Search .......................... 436/85, 161, 164, 436/121; 422/55, 59, 70, 82.05, 82.01; 356/300, 301; 250/339.08, 339.12; 702/28

(56) References Cited

U.S. PATENT DOCUMENTS

| | | | | |
|---|---|---|---|---|
| 4,460,750 A | * | 7/1984 | Thiersault et al. | 525/333.8 |
| 5,039,614 A | | 8/1991 | Dekmezian et al. | 436/43 |
| 5,071,913 A | * | 12/1991 | Powers et al. | 525/87 |
| 5,151,474 A | | 9/1992 | Lange et al. | 526/60 |
| 5,675,253 A | * | 10/1997 | Smith et al. | 324/306 |
| 5,700,895 A | | 12/1997 | Kanda et al. | 526/348 |
| 6,072,576 A | * | 6/2000 | McDonald et al. | 356/300 |

FOREIGN PATENT DOCUMENTS

JP 11060711 * 3/1999

OTHER PUBLICATIONS http://pep.sric.sri.com/Public/Reports/Phase_95/RP019F.html "Process Economics Program Report 19".*
http://wwwchem.csustan.edu/Tutorials/INFRARED.HTL "Interpretation of Infrared Spectra".*
Baum et al. "Tests on fully synthetic hydrocarbon waxes", Chem. Spec. Mfr. Ass., Proc. Mid-Year Meet. (1971), 57, 160–4.*
Stark "Near–infrared spectroscopy: the new FT frontier –spectroscopic and chemometric considerations", Proc. SPIE–Int. Soc. Opt. Eng. (1992), 1575(Int. Conf.Fourier Transform Spectrosc., 8th, 1991), 70–86.*
Parker et al. "Vibrational Absorption Intensities in Chemical Analysis, Part 9. The Near–Infrared Spectra of Methyl Branched Alkanes", J. Phys. Chem. A (1997), 101(50), 9618–9631.*
"Characterization of Short Chain Branching in Polyethylene Using Fourier Transform Infrared Spectroscopy" (Blitz, J. P. and McFaddin, D. C., J. Appl. Polym. Sci., 51, pp. 13–20, 1994).

* cited by examiner

*Primary Examiner*—Jill Warden
*Assistant Examiner*—Yelena Gakh
(74) *Attorney, Agent, or Firm*—Kilpatrick Stockton LP (57) ABSTRACT

A method of determining the proportion of short-chain branching in an olefin copolymer process stream is disclosed. The short-chain branching may also be determined as a function of molecular weight in a sample having a range of molecular weights. In the method, at least two olefin copolymer training samples are provided. The respective samples have different, known proportions of short-chain branching. The infrared (e.g. FT-IR) absorbance spectra of the training samples in a wavenumber range are obtained. Calibration information is determined from the training samples by chemometrically correlating the differences in the infrared absorbance spectra of the training samples to the differences in the degree of short-chain branching in the training samples. This step generates calibration information that allows the degree of short-chain branching in a sample to be determined once its infrared absorbance spectrum is obtained. A method for determining the statistical error in the measurement of short-chain branching in an olefin polymer sample as a function of its molecular weight distribution is also disclosed.

35 Claims, 6 Drawing Sheets

$$\text{Estimated Error} = 1.89 \times \left(\sqrt{\text{spectral area}}\right)^{-1} - 0.58$$

MEASUREMENT OF SHORT CHAIN BRANCHING IN OLEFIN COPOLYMERS USING CHEMOMETRIC ANALYSIS

CROSS-REFERENCE TO RELATED APPLICATIONS

Not applicable.

STATEMENT REGARDING FEDERALLY SPONSORED RESEARCH OR DEVELOPMENT

Not Applicable.

BACKGROUND OF THE INVENTION

The invention relates to the measurement of short chain branching in an ethylene 1-olefin copolymer as a function of its molecular weight. More particularly, the invention relates to such a measurement carried out by combining size exclusion chromatography, infrared (such as Fourier transform-infrared—"FT-IR") spectrophotometry, and chemometric analysis.

One property of synthetic polymers, such as olefin copolymers, is that these macromolecules have a molecular weight distribution—some of the polymer chains are longer than others.

An olefin copolymer also can be characterized by its degree of short-chain branching. The degree of short-chain branching can be determined by determining the number of methyl groups per 1000 carbon atoms in the sample. Given the average molecular weight of the sample, the number of methyl groups attributable to the ends of the polymer backbones can be calculated and subtracted from the number of methyl groups per 1000 carbon atoms to determine the number of methyl groups resulting from side branching. Each n-alkyl side chain has one methyl group.

In addition, an olefin copolymer can be characterized by the degree of short-chain branching as a function of its molecular weight distribution. In other words, a polymer can be characterized according to how many side chains are present on low-molecular weight polymer chains versus high-molecular weight polymer chains in a single bulk copolymer sample.

Information about the degree of short-chain branching ("SCB") of an olefin copolymer, expressed as a function of the molecular weight distribution ("MWD") of the copolymer, is useful for optimizing various properties of the olefin copolymer. Short-chain branching of the copolymer as a function of its molecular weight distribution affects such properties as the density, solvent extractables, and stress crack resistance of olefin copolymers. With this short-chain branching information in hand, the resin designer can modify the olefin copolymer polymerization process to optimize these properties of the resulting copolymer product.

The conventional analysis of short chain branching in an ethylene 1-olefin copolymer as a function of its molecular weight distribution involves solvent fractionation and subsequent characterization by NMR spectroscopy. Although the resulting values for short-chain branching distribution ("SCBD") are highly accurate, gathering the wanted information is labor and time intensive.

Chemometric analysis is a multivariate statistical technique of mathematically treating data from a plurality of measurements to improve the selectivity of the analytical results. See, for example, Stetter, J. R., Jurs, P. C., and Rose, S. L., Anal. Chem. Vol. 58, pp. 860–866 (1986), cited in U.S. Pat. No. 4,874,500. Also, see the text Chemometrics-a Practical Guide, by K. R. Beebe, R. J. Pell, and M. B. Seasholtz, Wiley, N.Y., 1998.

The inventors are not aware that chemometric analysis has been used to assist the determination of the degree of short-chain branching in a sample as a function of its molecular weight.

U.S. Pat. No. 5,700,895 (the '895 patent) discloses a method to measure the coefficient of variation of chemical composition distribution, $C_x$, and claims an ethylene-α-olefin copolymer having $C_x$ of 0.40 to 0.80 among five parameter limitations. The method (column 12, lines 30–67 & column 13, lines 1–37) includes FT-IR measurement of temperature rising elution fractions ("TREF" fractions) at each of 39 temperatures in the range −10 to 145° C. Chemical composition distribution, i.e. short chain branching obtained from spectral peak areas over the interval from 2983 to 2816 cm$^{-1}$ (SCB$_i$), is plotted as a function of elution temperature.

The '895 patent does not disclose using size-exclusion chromatography ("SEC") for fractionation or chemometric analysis for comparison of FT-IR curves. A TREF analysis involves the separation of a sample into fractions based on their differences in solubility in a solvent at different temperatures. Since both the molecular weight of a fraction and its degree of branching have impacts on its solubility, this technique does not separate the respective contributions of these two factors. This technique thus does not allow one to determine the degree of branching as a function of molecular weight. This technique also does not provide information on the statistical error of the results. This technique is also laborious.

U.S. Pat. No. 5,039,614 (the '614 patent) discloses a method to form solute films from solutions originating from fractionation based on a combination of physical and chemical property differences of ethylene/propylene copolymers (see claims 1 & 6 of the '614 patent). The films are obtained by rapid evaporation of solvent fractions from a gel permeation chromatography ("GPC") column. FT-IR data on the films characterizes the composition distribution of each polymer fraction. This is exemplified for two ethylene/propylene copolymer resin ("EPR") samples (column 8, lines 19–20). Chemometric analysis is neither suggested nor disclosed. The '614 patent discloses the formation of a polymer film by solvent evaporation before use of FT-IR to measure co-monomer incorporation.

U.S. Pat. No. 5,151,474 discloses and claims an ethylene polymerization process control method that uses FT-IR or other methods (column 4, lines 3–51) and chemometric analysis (column 4, lines 52–57) to measure the proportion of ethylene and 1-octene in a heptane solvent. There is no suggestion of polymer fractionation or a branching measurement.

Blitz, J. P. & McFaddin, D. C., "Characterization of Short Chain Branching in Polyethylene Using Fourier Transform Infrared Spectroscopy", J. APPL. POLYM. SCI. 1994, 51, 13–20, discloses the use of methyl and methylene rocking bands in the infrared spectrum to distinguish and quantify methyl, ethyl, butyl, hexyl and isobutyl branches in linear low-density polyethylene ("LLDPE"). There is no suggestion of polymer fractionation.

Eric T. Hsieh, Chung C. Tso, Jim Dyers, Timothy W. Johnson, Qiang Fu, and Stephen Z. D. Cheng, "Intermolecular Structural Homogeneity of Metallocene Polyethylene Copolymers," J. MACROMOL. SCI.-PHYS. B36(5), 615–628 (1997) discloses measurement of SCB distribution of polymer blends using cross fractionation and $^{13}$C NMR (carbon-13 nuclear magnetic resonance).

The conventional methods for fractionating polyolefins are laborious and time-consuming. For example, a single typical cross-fractionation analysis may require 40 to 50 different samples to be processed. Because each sample requires a minimum of 24 hours to process, just the separation step alone requires at least 40 days. Furthermore, an additional 24 hours is needed to analyze each sample by NMR, thereby requiring another 40 days to complete the analysis. The cross-fractionation technique also has the disadvantage of not providing a determination of the statistical error arising from the analysis, as a function of polymer chain length.

BRIEF SUMMARY OF THE INVENTION

One object of the invention is to obtain short-chain branching information about a sample as a function of its molecular weight distribution.

Another object of the invention is to provide short-chain branching distribution information about a sample in a relatively short time, so the information can be collected, analyzed, and used to control the process represented by the sample more quickly and less expensively.

An additional object of the invention is to provide short-chain branching information by a highly mechanized method that directly feeds a sample to an integrated analytical machine.

Still another object of the invention is to provide additional and more timely information about the relation of short-chain branching to molecular weight in polyolefins that are being produced. This information allows a resin designer to adjust the resin density and processing properties to desired values.

Yet another object of the invention is a method of determining the magnitude of the statistical error in the degree of short-chain branching, as a function of the molecular weight distribution. In other words, one can separately determine the amount of random error to be assigned to short-chain branching data at a given molecular weight.

One or more of the preceding objects, or one or more other objects which will become plain upon consideration of the present specification, are satisfied in whole or in part by the invention described herein.

One aspect of the invention, which satisfies one or more of the above objects in whole or in part, is a method of determining the short-chain branching distribution in a hydrocarbon sample.

At least two hydrocarbon training samples having different, known degrees of short-chain branching are provided. Infrared (such as FT-IR) absorbance spectra of the training samples are obtained. The spectra are examined to find at least one parameter that correlates with the known difference in the degree of short-chain branching among the training samples. The parameter can be found, for example, by chemometric analysis. Chemometric analysis is used to define a mathematical relationship between the value of the selected parameter and the degree of short-chain branching in the training samples.

A hydrocarbon test sample requiring analysis is provided. The values of the parameter found by analysis of the training samples are measured for the test sample. The mathematical relationship found by analysis of the training samples is applied to these parameter values for the test sample. As a result, the degree of short-chain branching in the test sample is determined.

The test sample is optionally treated to isolate at least one fraction having a particular molecular weight range (and optionally more fractions having different molecular weight ranges). The molecular weight range and the degree of short-chain branching in the fraction can then be determined.

Another aspect of the invention is a method of determining the short-chain branching distribution in a hydrocarbon sample as a function of its molecular weight distribution. In this method, a mathematical relationship is defined between the infrared (such as FT-IR) absorbance values of a test sample at 3000 to 2870 cm$^{-1}$ and the number of methyl groups per 1000 carbon atoms in the olefin copolymer sample.

An olefin copolymer test sample is isolated into at least one fraction having a particular molecular weight range. The infrared spectrum of the fraction is measured from about 3000 to about 2870 cm$^{-1}$ for the fraction. The spectral data may also be preprocessed using a variety of mathematical algorithms such as but not limited to data smoothing, baseline corrections, application of derivatives, and mean centering. A further mathematical relationship is then applied to the fraction to determine the degree of short-chain branching in the fraction, using an algorithm typically supplied by the chemometric software. The short-chain branching value given as such is for that particular molecular weight range of which the fraction is composed.

Still another aspect of the invention is a method for determining the statistical error in the measurement of short-chain branching in an olefin polymer sample as a function of its molecular weight distribution.

In this aspect of the invention, multiple replicates of an olefin polymer sample are provided. ("Multiple," in this context, means enough replicates to allow the chosen statistical analysis to be done. As a general rule, the more replicates are provided and analyzed, the more accurate the statistical analysis will be.)

Spectra of the replicate sample fractions are obtained in a wavenumber range useful for determining their degrees of short-chain branching. The degrees of short-chain branching in the replicate sample fractions are determined by analysis of the spectra. The statistical errors in the short-chain branching results in the replicate sample fractions are determined, as a function of molecular weight. The areas of the spectra of the replicate sample fractions, as a function of molecular weight, are also determined.

The statistical errors and areas for the respective fractions are then correlated by finding values of the slope m and intercept b in the following equation that at least approximate the relation between the statistical error and the area of the spectra for the respective replicate sample fractions:

$$E = mA^{-\frac{1}{2}} + b$$

In this equation, E is the statistical error for a sample fraction having a particular molecular weight, A is the area of the spectrum of the sample fraction, and m is the slope and b is the intercept. This equation can be solved by the chemometric method of partial least squares analysis.

A significant advantage of the present invention is that an analysis of the degree of short-chain branching in a sample can be carried out relatively quickly (in minutes) and with far less effort than before. This advantage allows the degree of short-chain branching in polymerization products, as a function of molecular weight, to be measured many times daily in the ordinary course of production, if desired. As with any process, it is advantageous to be able to provide timely, frequent information about the status of the reaction or other processing of an olefin copolymer process stream so the process conditions can be maintained within more precise specifications than before. Also, short-chain branching information can be gathered at lower cost than before. In addition, the analysis can be more statistically sophisticated than before. The statistical error can be determined as a function of the molecular weight distribution of the sample.

As a result, more accurate information can be obtained respecting whether a difference between two analyses is statistically significant, without the need to do replicate analyses and calculate the degree of statistical error each time the analysis is performed.

BRIEF DESCRIPTION OF THE SEVERAL VIEWS OF THE DRAWING

FIG. 11 represents the results of Example 3 in this specification.

DETAILED DESCRIPTION OF THE INVENTION

While the invention will be described in connection with one or more embodiments, it will be understood that the invention is not limited to those embodiments. On the contrary, the invention includes all alternatives, modifications, and equivalents as may be included within the spirit and scope of the claims at the end of this specification.

In the disclosed embodiment of the invention, short-chain branching in an ethylene 1-olefin copolymer sample is determined as a function of the molecular weight distribution of the sample using a combination of size exclusion chromatography, Fourier-transform infrared spectrophotometry (FT-IR), and chemometric analysis.

The method is carried out, in essence, as described in the Summary section above.

Analytical Instrument

Figure 1:
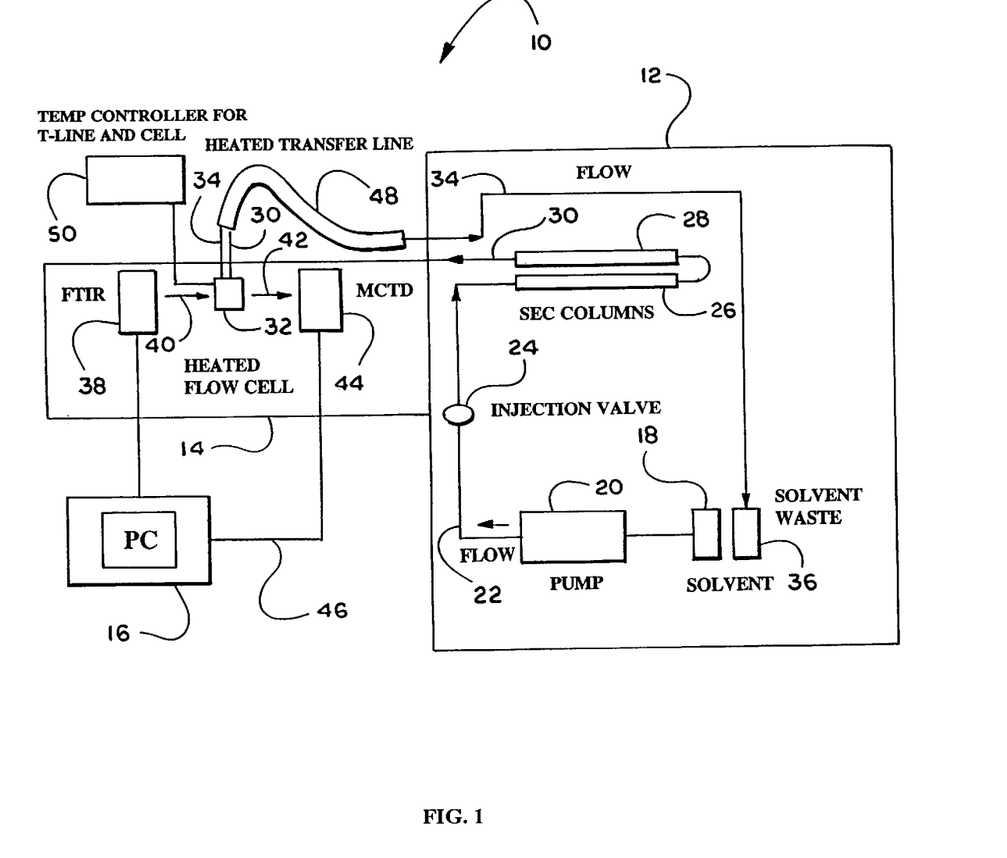
FIG. 1 is a schematic view of an integrated size-exclusion chromatography and FT-IR unit useful for practicing the present invention.

Suitable apparatus for carrying out the present analysis is illustrated in FIG. 1. A SEC-FT-IR unit 10 is provided that integrates a size-exclusion chromatography (SEC) apparatus 12 with a Fourier transform infrared spectrophotometer (FT-IR) 14. The apparatus is controlled by and the data is outputted to a computer 16. The computer 16 is programmed with chemometric software, as well as the software needed to operate the apparatus, carry out calculations, display results graphically, store results on a suitable medium, and perform other useful operations.

The SEC apparatus 12 includes a solvent source 18, a pump 20, conduits such as 22, an injection port 24, first and second chromatography columns 26 and 28 and a fraction effluent line 30. A sample to be fractionated in the SEC is introduced at the injection valve 24, where it is entrained in a flow of solvent taken from the solvent source 18 by the pump 20. The pump 20 pumps the solvent and entrained sample through the conduits such as 22 and the chromatography column, here the series-connected columns 26 and 28, of the apparatus. Here, a PL 210 gel permeation chromatography (GPC) unit (Polymer Laboratories) equipped with two Linear Mixed B columns (Polymer Laboratories) was used, with trichlorobenzene as an elution solvent.

As will be understood by the skilled person, the elution or travel rate of each molecule of the sample in the columns 26 and 28 varies according to its molecular weight. A smaller molecule in the sample travels through the columns 26 and 28 more slowly than a larger molecule of the same general kind, under the same conditions. Thus, the various molecules in a sample (if all are introduced at the same time) will separate according to their molecular size as they traverse the column. The largest fractions come through first, and the smallest fractions come through last. By measuring the elution time (time that elapses between the time when the sample to be analyzed is injected into the injection valve 24 and the time when it reaches a detector—in this case, the FT-IR apparatus described in the next paragraph), the molecular weight of a sample can be calculated through the use of elution times generated from analyses of samples with known molecular weights. The latter sets of samples are commonly referred to as molecular weight calibration standards.

The FT-IR apparatus 14 includes a source line coinciding with the fraction effluent line 30 that passes the fractionated sample effluent from the SEC column 28 to a flow cell 32. After passing through the flow cell 32, the sample traverses a waste effluent line 34 and is conveyed to a storage tank 36. An FT-IR infrared light source 38 passes infrared light 40 of the wavenumbers in the spectrum to be measured through the sample in the cell 32. The sample absorbs the light of different wavenumbers to different degrees, characteristic of its structure. Any light that is not absorbed is transmitted as an effluent beam 42 to a detector 44 which measures how much light of each detected wavenumber was absorbed by the sample. This measurement is reported through the data line 46 to the computer 16, which stores and processes the data.

In the equipment of FIG. 1, provisions are made to heat the flow cell 32, and the effluent lines 30 and 34 are protected by a jacket 48 that is also heated. The elevated temperature of the heated lines and cell is maintained by a temperature control 50.

As will be appreciated by a skilled person, other sample fractionation methods than size-exclusion chromatography can be used. For example, fractional distillation may be used to separate the components. In addition, if the process being measured itself fractionates the fed material, as with a fractional distillation process stream, samples of different fractions can be used without further fractionating them using chromatography.

Also, other chromatographic techniques than size exclusion chromatography can be used. For example highpressure liquid chromatography can be used in the context of the present invention. In this apparatus in particular, gel permeation chromatography is used.

A less preferred way to routinely carry out the separation, because it is laborious, is by manual cross-fractionation of samples using a solvent/non-solvent pair, as in the prior art. This technique may, however, be selectively useful for analyzing low volume fractions of a sample or to verify or spot-check results obtained by the present SEC-FT-IR method or other highly automated methods.

Further, other analytical tools than FT-IR can be used to carry out the present invention. For example, dispersive (i.e., not Fourier-Transform) IR is acceptable, though FT-IR is far more convenient. In principle, near-IR, either dispersive or Fourier Transform, might be used also, though the short sample path in the present method would give a signal with relatively low signal-to-noise ratio, decreasing the precision of the results. Other suitable spectroscopy equipment is described in U.S. Pat. No. 5,151,474, col. 4, lines 3–21, which is incorporated here by reference.

Chemometrics software is commercially available. The inventors contemplate that any suitable program or combination of programs may be used. One suitable program is Pirouette® for Windows Comprehensive Chemometrics Modeling Software, sold by Infometrix, Inc., Woodinville, Wash.

Test Sample Selection

The present invention is contemplated to be useful for analyzing hydrocarbons for their branching distribution over a molecular weight range. Common examples of hydrocarbons for which branching information is useful include olefin copolymers and polymer blends with densities ranging from about 0.8 to about 0.96. The polymer blends can be blends of two or more polymeric materials, each independently selected from homopolymers and copolymers.

Short-chain branching distribution may also be studied in polymers of higher olefins, such as polypropylene, polybutylene, polyisoprene, and others, or in naturally derived materials such as fatty acids and petroleum fractions. The present invention is not limited to a particular type of test sample.

Training Sample Selection and Characterization

In a chemometric analysis, data obtained from a series of at least two training samples having different, known compositions can be studied to ascertain interrelationships between the data and the known sample characteristics. More usually, more than two samples are studied in a single analysis. Alternatively, at least 5 samples, or at least 10 samples, or at least 20 samples, or at least 30 samples, or at least 40 samples, or at least 50 samples can be analyzed at once. The limit to the number of samples that can be analyzed at once usually is dictated by limitations of the software and computer hardware employed. No specific upper limit to the number of samples to be used is contemplated.

Normally (as here), a range of training samples having different compositions is tested so the differences in the data obtained for the respective samples can be evaluated to find changes in a pertinent dependent variable arising from changes in an independent variable. One can, however, employ a set of training samples that include some duplicate, triplicate, or more redundant samples. The inclusion of redundant training samples in a set that also includes many diverse training samples may reduce the statistical error. Training samples optionally can be samples characterized in prior work, the literature, by interpolation or extrapolation from other training samples, or other sources, as opposed to samples that are made physically available.

Another issue is the nature of the training samples selected. Training samples normally will closely resemble the desired test samples, so the properties of the test samples and the training samples can readily be compared. The set of training samples should include members having a range of properties that goes beyond the expected properties of the test samples. Selecting a broad range of training samples will allow a more robust model to be developed, so the data obtained from the training samples can be used for samples that may have properties somewhat different from the expected ones.

Selecting a broad range of samples also allows the use of interpolation instead of extrapolation to relate the properties of the training samples to the test samples. For example, assume the test sample is expected to have 2–10 short-chain branches per 1000 carbon atoms. A suitable range of test samples might be 25 training samples having different degrees of short-chain branching, bracketing the expected range of 2–10 branches. For example, the range of test samples might have from 0.5 branches to 15 branches per 1000 carbon atoms. These numbers are provided as an example, and do not limit the invention.

A suitable selection of training samples for analysis of a particular property can be made by blending in different proportions a first material that has a high degree of the particular property and a second material that has little or none of the particular property to be evaluated. To do this, the training samples must be analyzable for the particular property. For short-chain branching studies, the proportions of short-chain branching in the constituents of the training samples can be determined by $^{13}$C-NMR.

The training samples can, but need not, be made by separating fractions of a test sample. One advantage of the present invention is that this painstaking separation optionally can be avoided by using training sample constituents that are unfractionated solvents, oligomers, and polymers having different degrees of short-chain branching (determined by measurement or calculation).

For the present purposes, an "oligomer," or "hydrocarbon oligomer," is defined as a material containing hydrocarbon chains ranging from the molecular weight of a liquid or waxy solid alkane, on the low end, to the molecular weight approaching that of a high polymer, on the upper end. The exact molecular weight endpoints characterizing an oligomer are not critical, for the present purpose. An oligomer is simply a hydrocarbon material, other than a high polymer, with a relatively large proportion of methyl groups per 1000 total carbon atoms.

For example, assume a range of 25 training samples of ethylene copolymers having different degrees of short-chain branching from 0.5 branches to 15 branches per 1000 carbon atoms is contemplated. The first and last training samples can respectively be: (1) a first ethylene copolymer having 0.5 branches per 1000 carbon atoms, and (2) a second ethylene copolymer having 15 branches per 1000 carbon atoms. These first and second materials can also be blended in 23 different, regularly varying proportions to make 23 additional training samples. The 23 blended training samples fill out the range between the first sample having 0.5 branches and the last sample having 15 branches per 1000 carbon atoms.

The inventors also contemplate that materials other than those of the test samples can be used as training samples or constituents of training samples. For example, if the test sample is an ethylene copolymer to be analyzed for its degree of short-chain branching, one of the constituents of the training samples can be a highly branched ethylene copolymer, and the other constituent of the training samples can be a polyethylene homopolymer.

In the specific instance of measuring the degree of short-chain branching in an ethylene copolymer, exemplary training samples can have different numbers of methyl groups per 1000 carbon atoms. One example of a suitable range of branching in training samples is a range of from about 0 to about 85 methyl groups per 1000 carbon atoms.

Analytical data for the training samples can be measured, obtained from literature values, derived from prior work, or obtained from a combination of sources. It is not an essential feature of this invention that the analytical data for the training samples must be experimentally obtained information. Alternatively, digital combinations of FTIR spectra could be used in part or exclusively to generate training sample spectra. Advantages may in some instances be realized, however, by obtaining at least some of the training sample data experimentally. If the same operator analyzes the training samples and the test samples in the same equipment, the respective data may be more comparable than might otherwise be the case. One can also archive training sample data or a chemometric model derived from the data for repetitive use.

In the present case, FT-IR absorbance spectra of the training samples were obtained experimentally.

Figure 4:
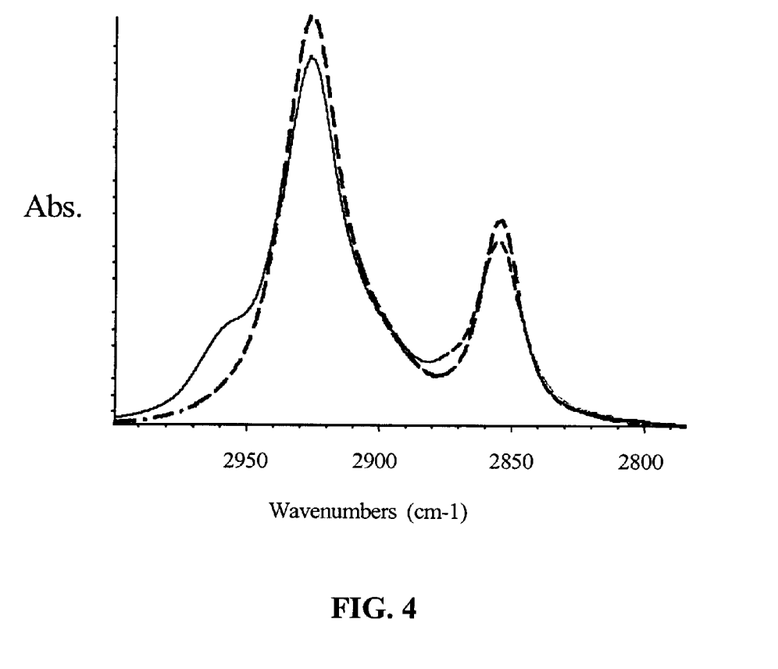
FIG. 4 is an FT-IR plot 52 of a hydrocarbon having 1.4 methyl groups per 1000 total carbon atoms. The plot 52 is superimposed on an FT-IR plot 54 of a hydrocarbon having 82.7 methyl groups per 1000 total carbon atoms. These superimposed plots show how the spectrum shifts as a function of the degree of short-chain branching. A larger number of methyl groups per 1000 total carbon atoms are indicative of a higher degree of short-chain branching.

FIG. 4 typifies spectral profiles obtained by analysis of training samples in a range from 1.4 to 82.7 methyl groups per 1000 carbon atoms. The shoulder at about 2958 cm-1 and the minimum between the principal peaks (which are $CH_3$ peaks) are higher and the two principal peaks (which are $CH_2$ peaks) are lower for the training sample with 82.7 methyl groups per 1000 total carbon atoms than for the training sample with 1.4 methyl groups per 1000 carbon atoms.

Other training samples can be used to obtain an even wider range of degrees of short-chain branching. For example, when a high-molecular-weight ethylene homopolymer has two methyl groups and an extremely high number of methylene groups, the difference between the two is so great that only the methylene groups are detectable. This training sample would thus have about 0 methyl groups, or side chains, per 1000 total carbon atoms.

Conversely, a propylene homopolymer has one methyl short-chain branch for every three carbon atoms—thus about 333 methyl groups per 1000 total carbon atoms. This training sample would have an extremely high degree of branching.

Chemometric Analysis of Training Samples

The FT-IR spectra and the NMR results or other branching information for the training samples are analyzed to find correlations between FT-IR spectral parameters and the degree of short-chain branching. Suitable parameters include shifts in absorbance at given wavenumbers for the respective training samples.

The analysis may conveniently be done in the apparatus described above in connection with FIG. 1, although other apparatus can also be used.

This analysis can be carried out using chemometric software. The chemometric software compares the spectra of the training samples. It finds correlations between spectral features, the degree of branching, and molecular weight. The software can perform a vast number of such comparisons. For example, the software can compare the absorbance of the respective samples at each wavenumber in a spectrum spanning more than 100 wavenumbers, until it finds wavenumbers whose absorbance can be correlated with the known short-chain branching distribution in a sample.

The wavenumber bands identified by the chemometrics program that have proven useful for determinations of short-chain branching include the C—H stretch band, which lies generally between about 3000 cm$^{-1}$ and about 2700 cm$^{-1}$, as well as particularly useful, narrower bands found within this general range. The C—H overtone bands falling within the same general wavenumber range are also contemplated for use in this invention. Many wavenumber bands found between an upper end at about 3000 cm$^{-1}$, alternatively about 2996 cm$^{-1}$, and a lower end at about 2700 cm$^{-1}$, alternatively about 2800 cm$^{-1}$, alternatively about 2820 cm$^{-1}$, alternatively about 2836 cm$^{-1}$, are contemplated to be useful. Wavenumber ranges between any of the upper end numbers and any of the lower end numbers stated above are contemplated to be useful. The band from 2996 cm$^{-1}$, to about 2836 cm$^{-1}$ is particularly useful for analysis of the samples in a trichlorobenzene solvent, which provides relatively little variation in absorbance over this wavenumber range. The solvent spectrum can be subtracted by conventional FT-IR software, so the solvent does not materially affect the reported absorbance of the sample.

Other contemplated wavenumber bands for measuring the degree of short-chain branching in an ethylene copolymer include the H—C—H bending band at about 1383–1377 cm$^{-1}$ and the —(CH$_2$)— rocking band at about 935–887 cm$^{-1}$. These are exemplary of bands suitable for investigating short-chain branching in solid ethylene copolymer samples by FT-IR analysis.

Once correlations with short-chain branching have been found, the chemometrics software can be used to find an empirical or other mathematical relationship between the value of the absorbance or some other peak parameter at the wavenumbers of interest and the degree of short-chain branching in the training samples. Although it is not appropriate in the context of chemometrics to speak of a relationship between, e.g., SCB and one or more peaks, what is possible is to define a relationship between points across a spectral range and the property of interest. The relevant equation is therefore $$M = \sum_{i=1}^{n} X_{V_i} A_{V_i}$$

where M is the number of methyl groups, A is the absorbance at a given wavenumber $v_i$, and X is a coefficient determined by the chemometric software, again at the given wavenumber.

Figure 2:
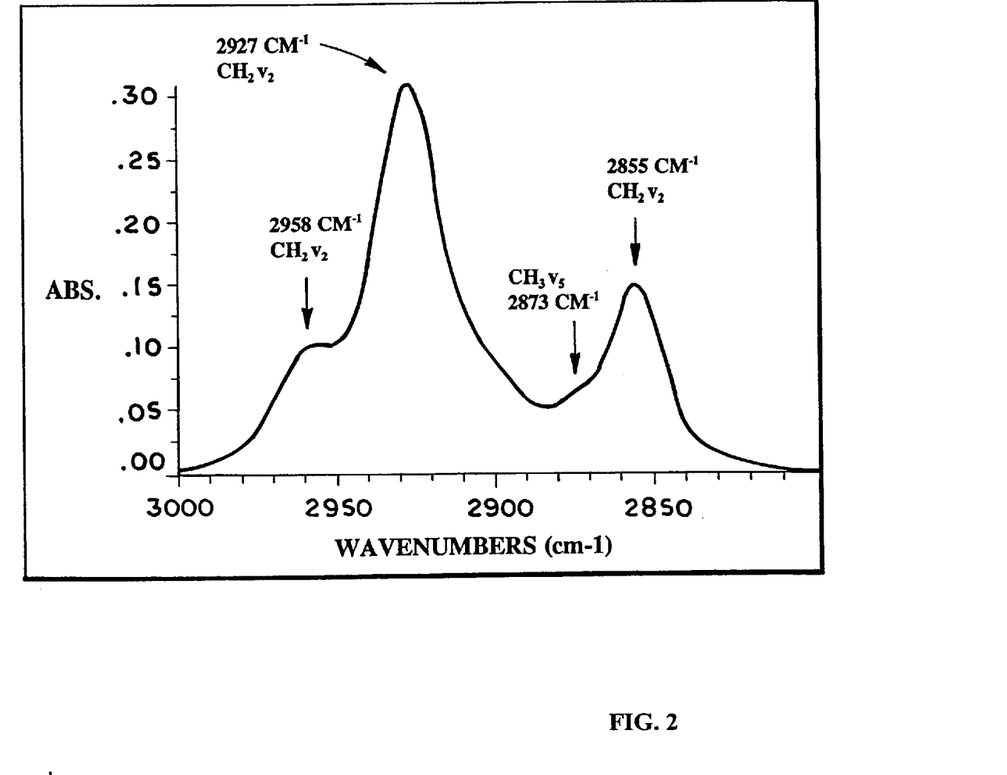
FIG. 2 is a plot of an FT-IR spectrum acquired from a GPC eluted hydrocarbon, showing fundamental vibrations present in the spectral region used to determine the methyl content in a sample across its molecular weight distribution.

FIG. 2 is an exemplary plot of an FT-IR spectrum of one fraction of a training sample at one particular molecular weight, with the fundamental stretching vibrations highlighted.

Figure 3:
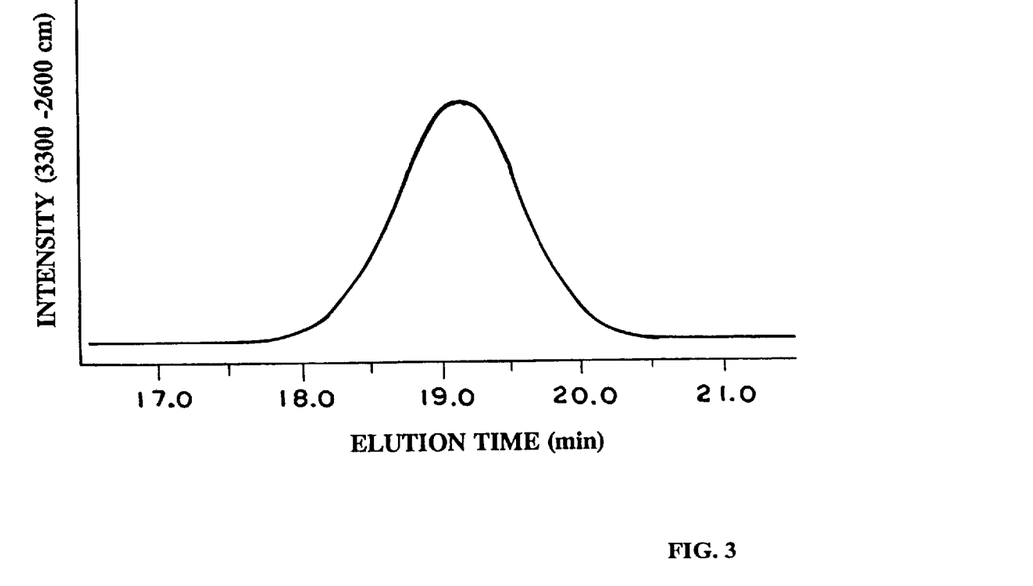
FIG. 3 is a plot of the concentration of the hydrocarbon sample of FIG. 2, measured as a function of elution time in a size exclusion chromatography instrument.

FIG. 3 is the concentration plot corresponding to the sample of FIG. 2. The concentration of the fraction is determined by calculating the root-mean-square absorbance of the FT-IR spectrum between predetermined upper and lower wavenumbers, and plotting it as a function of elution time. The predetermined upper and lower wavenumbers here are the upper and lower wavenumbers of the spectrum used for the short-chain branching analysis.

As a result of the analysis of each fraction of the training sample, a family of FT-IR absorbance spectrum plots and corresponding concentration/molecular weight plots is obtained.

FIG. 4 is an FT-IR spectrum plot 52 of a hydrocarbon having 1.4 methyl groups per 1000 total carbon atoms, superimposed on an FT-IR spectrum plot 54 of a hydrocarbon having 82.7 methyl groups per 1000 total carbon atoms. FIG. 4 shows how the absorbance spectrum shifts as a function of the degree of short-chain branching. Specifically, the absorbance 52 of the fraction containing 1.4 methyl groups per 1000 total carbon atoms is greater in the two principal $CH_2$ peaks at 2927 $cm^{-1}$ and 2855 $cm^{-1}$ and smaller in the two lesser $CH_3$ peaks at 2958 and 2873 $cm^{-1}$ than the absorbance 54 of the fraction containing 82.7 methyl groups per 1000 total carbon atoms. FIG. 4 is thus representative of the range of spectra making up this family of FT-IR absorbance spectrum plots.

The data from the training sample fraction spectra is analyzed to determine the methyl group concentrations in the fractions as a function of molecular weight, by comparison of the FT-IR spectra over the approximately 3000–2700 $cm^{-1}$ region as a function of elution time, and thus molecular weight.

Analysis of Test Samples

Another step of the analysis is to provide and analyze a hydrocarbon test sample. The analysis may conveniently be done in the apparatus described above in connection with FIG. 1, although other apparatus can also be used. In the analysis phase, the test sample is fractionated or otherwise isolated into relatively narrow molecular weight distribution slices, here by using SEC. Each slice is evaluated for the number of methyl groups per 1000 carbon atoms as a function of its molecular weight distribution, and for its relative weight in the complete sample, by comparing the test data with the chemometric calibration model. This information allows the calculation of the distribution of short-chain branches according to molecular weight in the complete sample.

Figure 5:
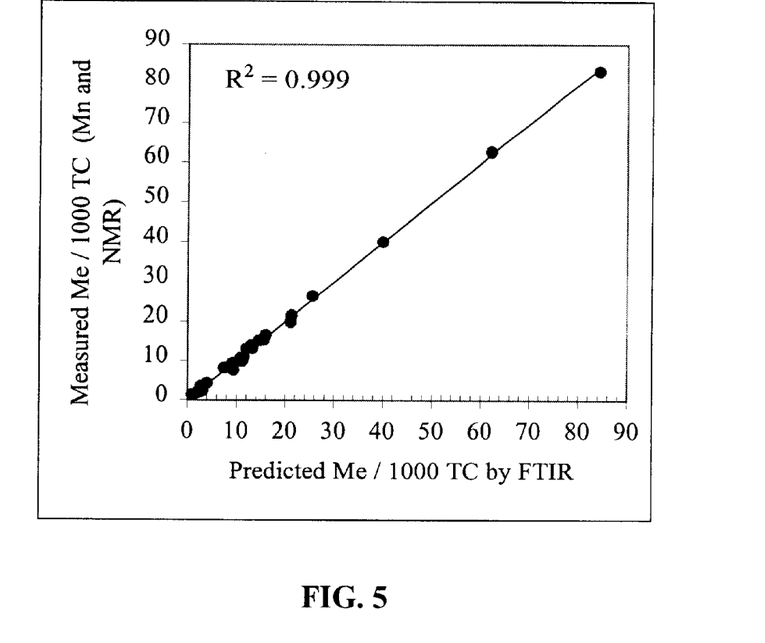
FIG. 5 is a calibration curve correlating changes in an FT-IR absorbance spectra with calculated or measured (by NMR) values for methyl groups per 1000 total carbon atoms for the 25 training samples of Example 1.

FIG. 5 is a calibration curve correlating changes in an FT-IR absorbance spectra with calculated or measured (by NMR) values for methyl groups per 1000 total carbon atoms for the 25 training samples of Example 1.

Figure 6:
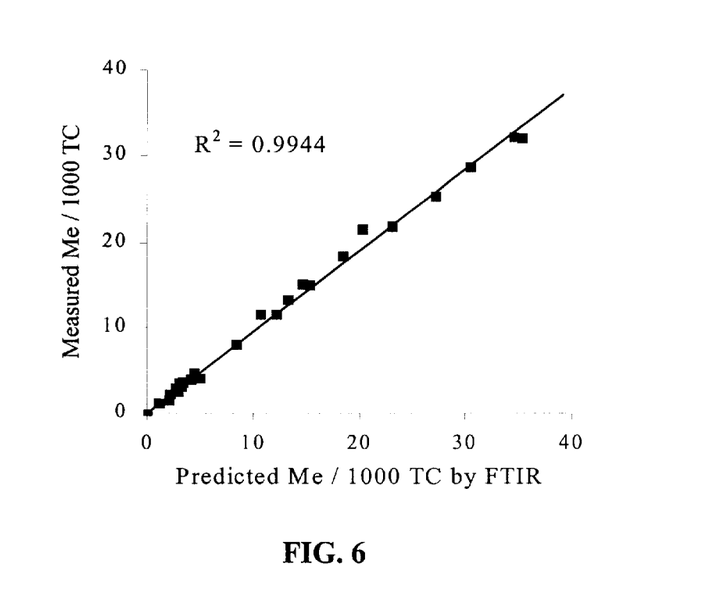
FIG. 6 is a validation plot correlating changes in an FT-IR absorbance spectrum with calculated or measured (by NMR) values for methyl groups per 1000 total carbon atoms for 24 additional samples used as a validation set.

FIG. 6 is a validation plot correlating changes in an FT-IR absorbance spectra with calculated or measured (by NMR) values for methyl groups per 1000 total carbon atoms for 24 additional samples used as a validation set.

Figure 7:
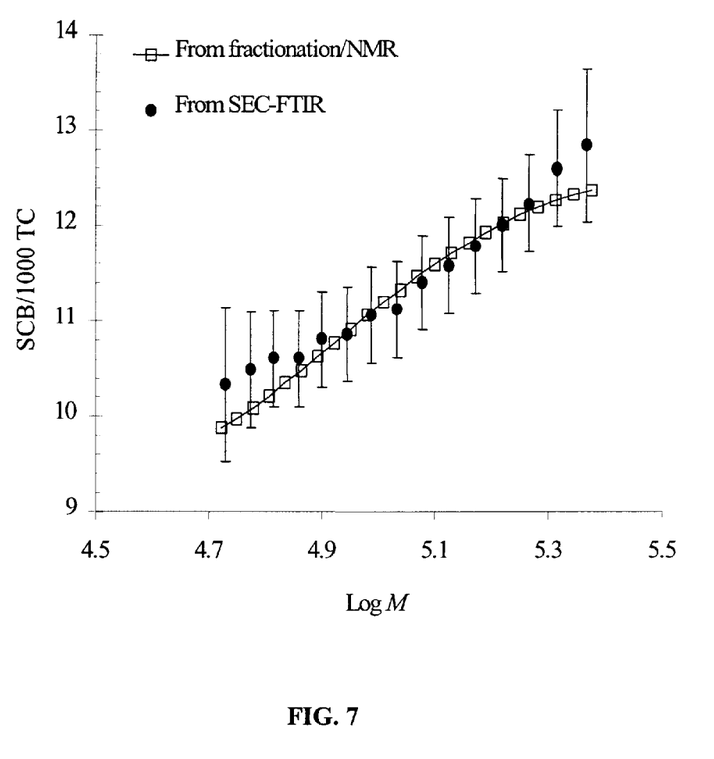
FIG. 7 is a plot of the amount of branching (expressed as methyl groups per 1000 total carbon groups) in an olefin copolymer fraction of a test sample versus its molecular weight distribution M. The circular data points are calculated from FT-IR spectra using the chemometric model according to the present invention. The "x" data points are determined by manual fractionation and NMR analysis of the sample, in a prior method. Most data points of the respective data sets lie essentially on a common line.

FIG. 7 is a plot of the amount of branching (expressed as methyl groups per 1000 total carbon groups) in an olefin copolymer fraction of a test sample versus its molecular weight distribution M. The circular data points are calculated from FT-IR spectra using the chemometric model according to the present invention. The "x" data points are determined by manual fractionation and NMR analysis of the sample, in a prior method. Most data points of the respective data sets lie essentially on a common line. FIG. 7 illustrates that the present invention provides essentially the same accuracy as the far more burdensome cross-fractionation/NMR method.

Figure 8:
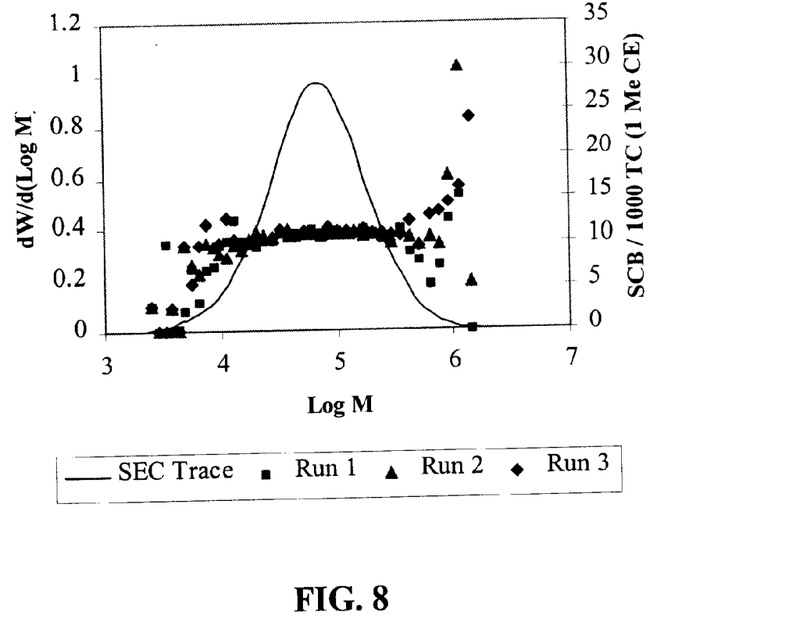
FIG. 8 is the initial characterization plot 62 of short-chain branching distribution versus molecular weight data points for all the fractions like the one characterized in FIG. 4. The plot 62 is superimposed on a Gaussian distribution plot 64 of concentration versus molecular weight for the same sample.

The results of the absorbance plots for each fraction of each test sample, as a function of molecular weight, can be summed up to determine the overall degree of branching in an olefin copolymer sample as a function of its molecular weight distribution. This summing up is indicated in FIG. 8. FIG. 8 is a plot 62 of many points representing the short-chain branching distribution versus molecular weight, superimposed on the corresponding Gaussian distribution plot 64 of concentration versus molecular weight for the same sample.

Figure 9:
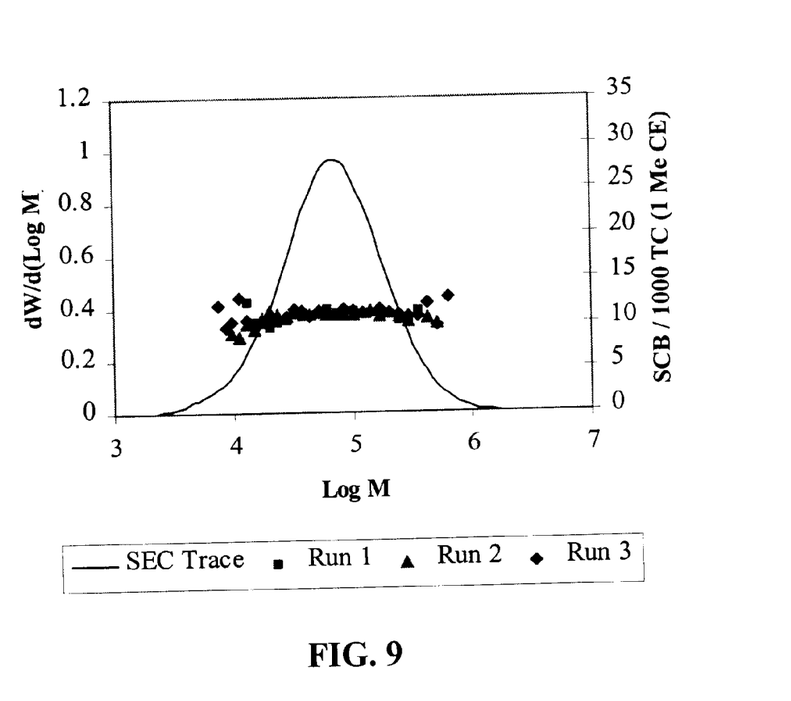
FIG. 9 is the representative data from FIG. 8 after removal of statistical outliers. The data is approximated by a plot 65 of short-chain branching distribution versus molecular weight data points for all the fractions like the one characterized in FIG. 4. The plot 65 is superimposed on a Gaussian distribution plot 64 of concentration versus molecular weight for the same sample.

FIG. 9 is the representative data from FIG. 8, after removal of statistical outliers. The resulting plot 65 is short-chain branching distribution versus molecular weight data points for all the fractions like the one characterized in FIG. 4. The plot 65 is superimposed on a Gaussian distribution plot 64 of concentration versus molecular weight for the same sample.

Figure 10:
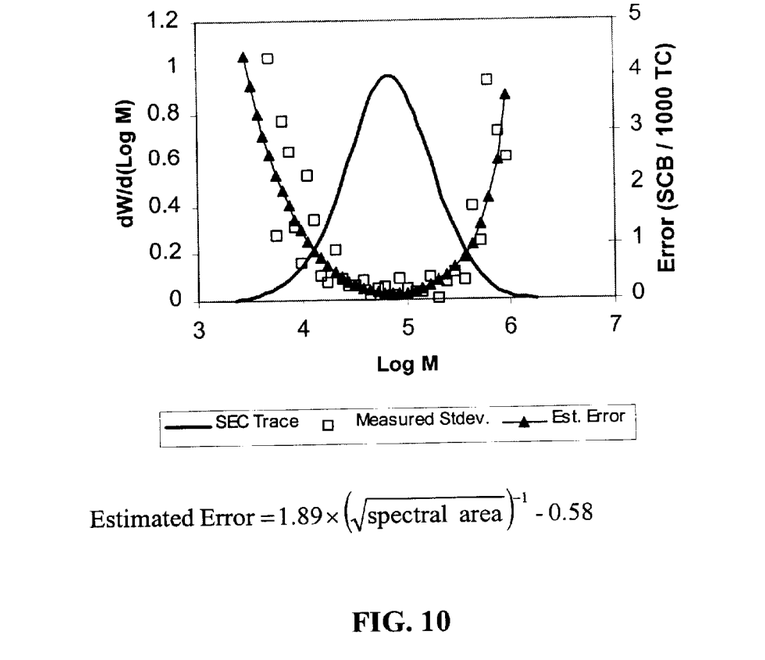
FIG. 10 is a concave-upward plot 66 of triangular points representing the empirically determined error for each SCB value versus molecular weight for the data illustrated in FIG. 6. The square points represent measured standard deviation values. A Gaussian distribution plot 64 of concentration versus molecular weight for the sample is superimposed.

FIG. 10 is a concave-upward plot 66 of statistically determined error from replicate runs for each SCB value versus molecular weight distribution for the data illustrated in FIG. 9. A Gaussian distribution plot 64 of concentration versus molecular weight for the sample is superimposed.

The plot 66 represents the empirically estimated error limits for measured short-chain branching levels in individual time slices of the chromatogram in terms SCB/1000 total carbons. This estimation was done by noting that the precision in replicate runs varied linearly with the inverse square root of the spectral area. The statistical errors and areas for the respective fractions are correlated by finding values of m and b in the following equation that at least approximate the relation between the statistical error and the area of the spectra for the respective replicate sample fractions:

$$E = mA^{-\frac{1}{2}} + b$$

In this equation, E is the statistical error for a sample fraction having a particular molecular weight distribution, A is the area of the spectrum of the sample fraction, and m and b are the slope and intercept.

A parameter other than the spectrum area A could alternatively be used in the above equation to carry out this error analysis. For example, the error analysis can be carried out based on spectral residuals, representing the differences between the expected spectrum and the actual spectrum of sample fractions Using this error method, the number of replicate runs can be reduced to zero in most cases. Although ASTM Method E 1655 can be used to estimate the error in individual data points predicted by chemometric methods, in this analysis it is inapplicable, since ASTM E 1655 assumes no concentration errors in the spectra measured. This is clearly not the case in this analysis, thereby showing an improvement of this invention over prior art.

To summarize, SEC-FT-IR analysis and chemometric software are used to characterize the short-chain branching distribution of olefin copolymer samples as a function of molecular weight. The 3000–2700 $cm^{-1}$ FT-IR spectral region or a subset of this region has been found to be suitable, as it minimizes the influence of the solvent employed here (trichlorobenzene), and was found to allow good correlation of short-chain branching with spectral characteristics. The inventors contemplate that other spectral regions may also or instead be employed, within the scope of the present invention. Other spectral regions are expected to be appropriate if the analytical conditions, such as the choice of solvent, the technique or equipment employed, or other factors are varied.

Frequent (several samples a day) SEC-FT-IR analysis of short chain branching distribution (SCBD) across the molecular weight distribution (MWD) can be demonstrated using several types of ethylene 1-olefin copolymers. Chromatograms can be generated using the root mean square absorbance over the 3000–2700 $cm^{-1}$ or other spectral region (i.e., FT-IR serves as a concentration detector). Spectra from individual time slices of the chromatogram are subsequently analyzed for co-monomer branch levels using chemometric techniques. This method enables one to quantify branching levels in polyolefins down to about 1/1000 total carbon atoms. Prior art describes measurements limited to 2/1000 C. Furthermore, one can estimate the error in the reported SCB content of each MW slice. The current method is expected to provide SCB profiles with sufficient precision to detect trends resulting from catalyst and process changes.

One contemplated variation on the present analysis is to differentiate between, and calculate the proportion of, different types of branching in a hydrocarbon sample, instead of merely determining the amount of branching. This may be done by providing training samples having different types and amounts of branching and identifying spectral differences that correlate with the amount of each particular type of branching. Chemometric analysis is again an appropriate way to identify these spectral differences. Once this has been done, the spectra of test samples can be conveniently analyzed for both different types and amounts of branching in a single analysis.

EXAMPLE 1

SEC-FT-IR Measurements of Training Samples 25 narrow molecular weight, solvent gradient fractions of ethylene 1-butene, ethylene 1-hexene, ethylene 1-octene copolymer and polyethylene homopolymers, as well as low molecular weight alkanes, were prepared for use as training samples. The samples had a molecular weight distribution, "MWD", of from about 1.1 to 1.3. The total methyl content of these samples ranged from 1.4 to 82.7 methyl groups per 1000 total carbons.

The methyl contents of the samples were calculated from their number average molecular weights ($M_n$) or measured using $^{13}$C-NMR spectroscopy. The $^{13}$C-NMR spectra were obtained on 15 wt. % samples in TCB using a 500 MHz Varian Unity Spectrometer run at 125° C. Methyl content per 1000 carbons by NMR was obtained by multiplying (x1000) the ratio of branching signals to total signal intensity.

The training samples were dissolved in trichlorobenzene (TCB) containing 0.034 wt. % BHT (a preservative) by heating the mixture for 2 hr. at 155° C. in a Blue M air convection oven. A PL 210 gel permeation chromatography (GPC) unit (Polymer Laboratories) equipped with two Linear Mixed B columns (Polymer Laboratories) was used for molecular weight determinations. Samples having a concentration of about 1.8 mg/mL concentration were eluted at 1 mL/min (ml./minute) using TCB as the mobile. The sample injection volume was 500 µL (microliters).

The effluent from the Mixed B columns was directed into an FT-IR machine. In this instance a Perkin Elmer model 2000 FT-IR spectrophotometer equipped with a narrow band mercury cadmium telluride (MCT) detector was used to obtain IR spectra. For this test, the samples were introduced from the chromatography column to the FT-IR detector via a heated transfer line and flow cell (KBr windows, 1 mm optical path and about 70 µL cell volume), in the apparatus shown in FIG. 1. The temperatures of the transfer line and flow cell were kept at 143±1° C. and 140±1° C., respectively. Background spectra were obtained using a solvent filled cell. All of the IR spectra were measured at 8 $cm^{-1}$ resolution (16 scans).

Chromatograms were generated using the root mean square absorbance over the 3000–2700 $cm^{-1}$ spectral region (i.e., FT-IR serves as a concentration detector). Molecular weight calculations were made using a broad molecular weight polyethylene standard.

Spectra from individual time slices of the chromatograms in the 3000–2700 $cm^{-1}$ spectral region generated were subsequently analyzed for co-monomer branch levels using chemometric techniques.

A calibration curve was generated from the spectra using Pirouette® chemometric software to correlate changes in the FT-IR absorbance spectra with calculated or measured (by NMR) values for methyl groups/1000 total carbon atoms for the 25 training samples (see FIG. 5). The software was employed under the conditions described above to generate the desired correlation data.

The calibration results were obtained for the spectral region between 3000 and 2700-$cm^{-1}$ to avoid the solvent interference in quantitative results for prediction of the measured sample spectrum. Preprocessing of spectral data included smoothing (9 pts.), baseline correction and normalization. Further preprocessing of the spectral data entailed taking the first derivative of the spectra and mean centering all data.

A four principal-component calibration model was calculated and optimized using the process of cross validation. $R^2=0.999$, where $R^2$ is the correlation coefficient for linear fit, and SECV=0.6, where SECV is the standard error of calibration, a chemometric parameter measuring how well the model fits the data used in the training set.

The calibration model was verified using 24 additional samples as a validation set. The predicted vs. actual values for the validation data showed excellent correlation ($R^2=0.994$) and exhibited a standard error of validation equal to ±0.5 methyl groups/1000 total carbons (see FIG. 6).

Short chain branching levels in the training samples were calculated by subtracting out methyl chain end contributions. The proportion of methyl chain ends was calculated using the equation:

$$Me_{ce}=C(2-V_{ce})/M$$

where: $Me_{ce}$ is the number of methyl chain ends per 1000 total carbons, C is a constant equal to 14000 (1000 times 14—the molecular weight of one $CH_2$ group), $V_{ce}$ is the number of vinyl terminated chain ends (1 for chromium catalyzed resins and 0 for Ziegler-Natta catalyzed resins), and M is the molecular weight calculated for a particular slice of the MWD.

EXAMPLE 2

Determination of Branching in a Sample From a Polymerization Process

The SCBD of a solvent gradient fraction of a sample from a process stream was measured across the MWD by correlating the SEC/FT-IR spectra obtained from the process stream sample with its SCBD, using the chemometric calibration method used and the correlation data obtained in Example 1. The results were compared to the SCB levels measured by NMR in cross-fractionated samples of the same SG fraction. As shown for this example, a good correlation was found to exist between the two methods. (See FIG. 7.) Both methods show the expected increase in branch content with increasing molecular weight based on the solvent/nonsolvent pair used for the solvent gradient fractionation. Although the rise in branching level in this sample was slight (~10 to 12 Me/1000 TC), the trend could be observed using the SEC-FT-IR method.

EXAMPLE 3

Figure 11:
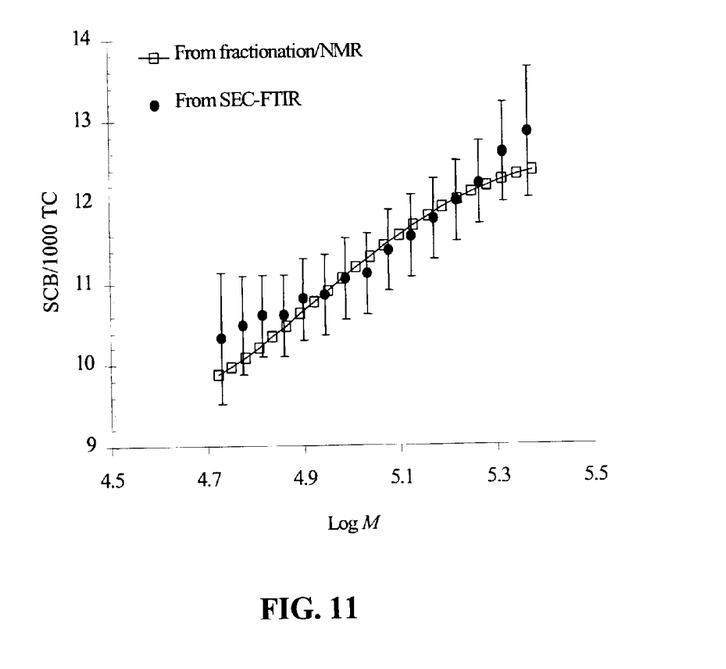
FIG. 11 is an SEC trace of a physical mixture of a homopolymer and a branched copolymer, also including plots representing the homopolymer contribution and the branched copolymer contribution to the SEC trace. Data points are provided representing the amount of short-chain branching over the molecular weight distribution, as calculated according to the present invention.

In this example, a low molecular weight homopolymer was mixed with a high molecular weight branched ethylene 1-hexene copolymer. Both resins were known to contain only methyl chain ends. The results are shown in FIG. 11. The SEC trace of the mixture is shown by the plot 70. The plot 72 represents the homopolymer contribution to the plot 70, and the plot 74 represents the branched copolymer contribution to the plot 70. The data points represent the short chain branching distribution of the sample, as a function of molecular weight, as determined by the present chemometric method.

The SCB levels and corresponding molecular weight results obtained from the SEC-FTIR analysis correlated well with the expected results for this sample. That is, branching was seen in the upper molecular weight portion of the sample. This example also illustrates the power of this method to elucidate the polymer architecture in multi-modal systems.

That which is claimed is:

1. A method of determining the short-chain branching distribution in a hydrocarbon sample, comprising:
   a) obtaining infrared absorbance spectra of at least two training samples having different, known degrees of short-chain branching;
   b) finding at least one parameter of said absorbance spectra that correlates with the known difference in the degree of short-chain branching between said at least two training samples;
   c) by chemometric analysis, defining a mathematical relationship between the value of said at least one parameter and the degree of short-chain branching in said training samples;
   d) providing a hydrocarbon test sample and isolating at least one fraction from the hydrocarbon test sample;
   e) determining the value of said at least one parameter for said at least one fraction; and
   f) applying said mathematical relationship to said parameter values for said at least one fraction, thereby determining the degree of short-chain branching in said at least one fraction.

2. The method of claim 1, wherein said hydrocarbon sample is an olefin copolymer.

3. The method of claim 1, wherein said hydrocarbon sample is a blend of at least two polymeric materials, each independently selected from homopolymers and copolymers.

4. The method of claim 1, wherein said hydrocarbon sample is a polymer having a density of from about 0.8 to about 0.96 g/cm$^3$.

5. The method of claim 1, wherein at least 10 of said hydrocarbon training samples are provided.

6. The method of claim 1, wherein at least 20 of said hydrocarbon training samples are provided.

7. The method of claim 1, wherein at least 30 of said hydrocarbon training samples are provided.

8. The method of claim 1, wherein at least 40 of said hydrocarbon training samples are provided.

9. The method of claim 1, wherein at least 50 of said hydrocarbon training samples are provided.

10. The method of claim 1, wherein at least one of said training samples is an unbranched hydrocarbon oligomer.

11. The method of claim 1, wherein at least one of said training samples is an ethylene homopolymer.

12. The method of claim 1, wherein at least one of said training samples is a branched olefin copolymer.

13. The method of claim 1, wherein at least one of said training samples is a branched alkane.

14. The method of claim 1, wherein the respective training samples have different numbers of methyl groups per 1000 carbon atoms, each number of methyl groups per 1000 carbon atoms falling within the range of from about 1 to about 85 methyl groups per 1000 carbon atoms.

15. The method of claim 1, wherein the respective training samples have different numbers of methyl groups per 1000 carbon atoms, each number of methyl groups per 1000 carbon atoms falling within the range of from about 0 to about 333 methyl groups per 1000 carbon atoms.

16. The method of claim 1, wherein the respective training samples have numbers of methyl groups per 1000 carbon atoms bracketing the numbers of methyl groups per 1000 carbon atoms expected in the sample.

17. The method of claim 1, wherein the infrared absorbance spectra are FT-IR absorbance spectra of said at least two training samples.

18. The method of claim 1, wherein the infrared absorbance spectra are measured at least in a C—H stretch band.

19. The method of claim 1, wherein the infrared absorbance spectra are measured at least in a C—H overtone band.

20. The method of claim 1, wherein the infrared absorbance spectra are measured at least in the band from about 3000 cm$^{-1}$ to about 2700 cm$^{-1}$.

21. The method of claim 1, wherein the infrared absorbance spectra are measured at least in the band from about 3000 cm$^{-1}$ to about 2800 cm$^{-1}$.

22. The method of claim 1, wherein the infrared absorbance spectra are measured at least in the band from about 3000 cm$^{-1}$ to about 2820 cm$^{-1}$.

23. The method of claim 1, wherein the infrared absorbance spectra are measured at least in the band from about from 2996 cm$^{-1}$, to about 2836 cm$^{-1}$.

24. The method of claim 1, wherein the step of finding at least one parameter of said spectra is carried out by using chemometric analysis to compare the known degree of short-chain branching to the respective degrees of absorbance in a spectrum of wavenumbers, in the respective training samples, until a statistically significant correlation is found between the relative absorbance of a training sample at a set of said wavenumbers and the degree of short-chain branching in the sample.

25. The method of claim 1, wherein said step of defining a mathematical relationship is carried out by the chemometric method of partial least squares analysis.

26. The method of claim 1, wherein the proportions of short-chain branching in at least some of said training samples are determined by $^{13}$C-NMR analysis.

27. The method of claim 1, wherein the isolation step comprises selecting from said test sample at least one fraction which gives at least one spectrum associated with a particular molecular weight range, wherein the molecular weight range and the value of said at least one parameter for said test sample are determined independently for at least two fractions.

28. The method of claim 27, wherein said isolation step is carried out by a chromatographic method.

29. The method of claim 28, wherein said chromatographic method is size-exclusion chromatography.

30. The method of claim 27, wherein the concentration of each fractions are determined by calculating the root-mean-square absorbance of the FT-IR spectrum between predetermined upper and lower wavenumbers as a function of elution time.

31. A method of determining the short-chain branching distribution in a hydrocarbon sample as a function of its molecular weight distribution, by defining a mathematical relationship between the infrared absorbance of an olefin copolymer test sample in a spectrum of from about 3000 to about 2870 cm$^{-1}$, and the number of methyl groups per 1000 carbon atoms in the olefin copolymer sample; comprising:
   a) providing an olefin copolymer test sample;
   b) isolating at least one fraction from said test sample;
   c) characterizing the molecular weight distribution of said at least one fraction;
   d) determining the infrared absorbance spectrum of said at least one fraction in said spectrum of from about 3000 to about 2870 cm$^{-1}$; and
   e) applying said mathematical relationship to said infrared absorbance spectrum, thereby determining the degree of short-chain branching in said olefin polymer test sample as a function of its molecular weight distribution.

32. A method for determining the statistical error in the measurement of short-chain branching in an olefin polymer sample as a function of its molecular weight distribution, comprising:
   a) providing multiple replicates of an olefin polymer sample;
   b) isolating from the respective replicate samples at least one fraction having a particular molecular weight distribution;
   c) determining the molecular weight ranges of the replicate sample fractions;
   d) obtaining infrared absorbance spectra of the replicate sample fractions in a wavenumber range useful for determining their degrees of short-chain branching;
   e) determining the degrees of short-chain branching in the replicate sample fractions, by analysis of said infrared spectra;
   f) determining the statistical error in the short-chain branching results in the replicate sample fractions, as a function of molecular weight distribution;
   g) determining the areas of the spectra of the replicate sample fractions, as a function of molecular weight; and
   h) finding values of m and b in the following equation that at least approximate the relation between the statistical error and the area of the spectrum for the respective replicate sample fractions:

$$E = mA^{-1/2} + b$$

where E is the statistical error for a sample fraction having a particular molecular weight, A is the area of the spectrum of the sample fraction, and m and b are the slope and intercept.

33. The method of claim 32, where E is the standard deviation of the short-chain branching results.

34. The method of claim 32, where the infrared spectra are FT-IR spectra.

35. The method of claim 34, where A is the root-mean-square absorbance of the FT-IR spectra between predetermined upper and lower wavenumbers.

* * * * *